United States Patent
Ducoroy et al.

(10) Patent No.: US 10,238,786 B2
(45) Date of Patent: Mar. 26, 2019

(54) LEUKOCYTE FILTRATION UNIT WITH REDUCED PLATELET ADHESION

(71) Applicant: MacoPharma, S.A.S., Mouvaux (FR)

(72) Inventors: Laurent Ducoroy, Lille (FR); Emilie Bessy, Sainte Maxime (FR); Gregory Henard, Lille (FR); Christophe Hupin, Salles (FR); Sonia Dakhli, Bordeaux (FR); Laurent Fouchet, Prignac et Marcamps (FR)

(73) Assignee: MACOPHARMA, S.A.S., Mouvaux (FR)

( * ) Notice: Subject to any disclaimer, the term of this patent is extended or adjusted under 35 U.S.C. 154(b) by 1042 days.

(21) Appl. No.: 14/227,561

(22) Filed: Mar. 27, 2014

(65) Prior Publication Data

US 2014/0291227 A1 Oct. 2, 2014

(30) Foreign Application Priority Data

Mar. 27, 2013 (FR) ...................................... 13 52779

(51) Int. Cl.
*A61M 1/36* (2006.01)
*B01D 39/16* (2006.01)
(Continued)

(52) U.S. Cl.
CPC ............ *A61M 1/36* (2013.01); *A61M 1/0218* (2014.02); *A61M 1/3633* (2013.01);
(Continued)

(58) Field of Classification Search
CPC .... B01D 2239/0414; B01D 2239/0421; B01D 2239/0471; B01D 2239/0478;
(Continued)

(56) References Cited

U.S. PATENT DOCUMENTS

| 4,936,998 A | 6/1990 | Nishimura et al. |
| 5,407,581 A * | 4/1995 | Onodera ............ B01D 39/1623 210/321.69 |

(Continued)

FOREIGN PATENT DOCUMENTS

| EP | 1230940 A1 | 8/2002 |
| EP | 1336417 A1 | 8/2003 |

(Continued)

OTHER PUBLICATIONS

English language machine translation of FR2892949, No Date, 12 Pages.*

(Continued)

*Primary Examiner* — Pranav N Patel
(74) *Attorney, Agent, or Firm* — Baker Botts L.L.P.

(57) ABSTRACT

A filtration unit to selectively remove leukocytes from fluids containing platelets and systems including a filtration unit are provided. In one embodiment, a filtration unit is provided including an outer casing enclosing a porous element which includes a leukocyte-removal medium with a coating. The coating includes a polymer containing a main hydrophobic chain and a hydrophilic poly(ethylene oxide) side chain and having a mass average molar mass in the range of from about 1,000 g/mol to about 20,000 g/mol. The hydrophilic poly(ethylene oxide) side chain includes from 9 to 50 ethylene oxide units, and the mass percentage of the poly (ethylene oxide) side chain is less than about 50% of the mass average molar mass of the polymer.

22 Claims, 2 Drawing Sheets

(51) Int. Cl.
*B01J 20/26* (2006.01)
*B01J 20/32* (2006.01)
*A61M 1/02* (2006.01)

(52) U.S. Cl.
CPC ........ *B01D 39/1623* (2013.01); *B01J 20/264* (2013.01); *B01J 20/3276* (2013.01); *A61M 2202/0439* (2013.01); *B01D 2239/0421* (2013.01); *B01D 2239/1216* (2013.01)

(58) Field of Classification Search
CPC ...... B01D 2239/492; B01D 2239/1216; B01D 39/1623; B01D 69/02; B01D 69/10; B01D 69/12; A61M 1/0218; A61M 1/36; A61M 1/3633; A61M 1/3679; A61M 2202/0439; A61M 2202/0427; A61M 2202/0057; B01J 20/264; B01J 20/3276
See application file for complete search history.

(56) References Cited

U.S. PATENT DOCUMENTS

| | | | | |
|---|---|---|---|---|
| 5,494,855 | A * | 2/1996 | Nohr | D01F 6/46 428/198 |
| 6,150,459 | A * | 11/2000 | Mayes | A61K 47/48169 435/325 |
| 2003/0059537 | A1* | 3/2003 | Chilkoti | B05D 1/283 427/256 |
| 2003/0150793 | A1* | 8/2003 | Verpoort | A61M 1/3633 210/489 |
| 2006/0207937 | A1 | 9/2006 | Bonaguidi et al. | |
| 2009/0159522 | A1* | 6/2009 | Marmey | A61M 1/0209 210/335 |
| 2012/0048798 | A1* | 3/2012 | Cheng | B01D 71/40 210/490 |

FOREIGN PATENT DOCUMENTS

| | | |
|---|---|---|
| EP | 1452193 A1 | 9/2004 |
| EP | 1553113 A1 | 7/2005 |
| EP | 2075018 A1 | 7/2009 |
| FR | 2892949 A1 | 5/2007 |
| JP | H0752776 A | 1/1995 |
| JP | 2003164521 A | 6/2003 |
| JP | 2006035090 A | 2/2006 |
| JP | 2008079890 A | 4/2008 |
| WO | 2007/054638 A1 | 5/2007 |

OTHER PUBLICATIONS

English language machine translation of JP H07-025776, No Date, 17 Pages.*

Matsuda, T. et al., "Surface coating of hydrophilic-hydrophobic block co-polymers on a poly(acrylonitrile) haemodialyser reduces platelet adhesion and its transmembrane stimulation" Biomaterials (Elsevier) vol. 15, No. 6 (May 1, 1994), pp. 417-422.

Search Report and Written Opinion issued in related French Patent Application No. 1352779, dated Feb. 4, 2014, 13 pages.

* cited by examiner

LEUKOCYTE FILTRATION UNIT WITH REDUCED PLATELET ADHESION

CROSS REFERENCE TO RELATED APPLICATION

This application claims the benefit of French application No. 1352779, filed Mar. 27, 2013, the entire disclosure of which is hereby incorporated by reference.

BACKGROUND

The present disclosure generally relates to the filtration of a fluid containing platelets. More specifically, the present disclosure relates to a filtration unit to selectively remove leukocytes from a fluid containing platelets, and systems comprising such a filtration unit.

Whole blood is formed of two types of components: first, blood cells comprising red blood cells, leukocytes and platelets, and second, plasma, which is a pale yellow liquid in which the blood cells are suspended.

Currently, only necessary blood components are transfused to patients. For example, only platelet concentrates are transfused to patients suffering from thrombocytopenia, who have a reduced amount of platelets in the blood.

It has been found that leukocytes have rather significant undesirable effects, which has led to attempts to eliminate them from blood components intended for transfusion. In fact, leukocytes increase the risk of immune rejection, such as graft-versus-host disease, and promote the transmission of infectious agents. It has also been demonstrated that leukocytes negatively affect platelet preservation.

To eliminate leukocytes from blood components intended for transfusion, filtration units enclosing a leukocyte-removal medium are generally used. In such units, the leukocyte-removal medium comprises one or more membrane(s) and/or one or more layer(s) of non-woven material made of a polymer material and treated to improve the rate of leukocyte removal, the recovery of the blood components, the priming time for filtration, and/or the selectivity of the filtration.

Such filtration units may improve the selectivity of the filtration, for example, by allowing platelets to pass through the leukocyte-removal medium. To eliminate leukocytes while still allowing the platelets to pass through, a number of polymer surface treatments of leukocyte-removal media have been proposed. For example, U.S. Pat. No. 4,936,998 describes a filter medium for selectively eliminating leukocytes. The filter medium is formed of fibers coated with a polymer containing non-ionic hydrophilic groups and basic functional groups containing nitrogen. Such a polymer is, for example, a copolymer of hydroxyethyl methacrylate and diethylaminoethyl methacrylate.

In addition, EP 1230940 describes a filter for eliminating leukocytes while allowing platelets to pass through the filter. The filter comprises a substrate, the surface of the substrate being at least 70% coated with a synthetic hydrophilic polymer having a mass average molecular mass between 300,000 and 3,000,000. As in document U.S. Pat. No. 4,936,998, the polymer is a copolymer containing non-ionic hydrophilic groups and basic functional groups containing nitrogen, obtained, for example, by copolymerization of hydroxyethyl methacrylate and diethylaminoethyl methacrylate. EP 1230940 also provides that when the filter is coated with a polymer having a mass average molecular mass below 300,000, the rate at which platelets pass through the filter is reduced.

JP 7-25776 proposes a filter for selectively eliminating leukocytes, comprising, on its surface, a polymer provided with a polyethylene glycol chain and hydrophobic portions. In EP 1452193, it is explained, however, that this polymer, due to the increased quantity (59-74 wt %) of ethylene oxide chains, poses the risk of eluting the polymer into the blood. To solve this problem, document EP 1452193 suggests using a polymer obtained from: (i) a hydroxyalkyl (meth)acrylate, (ii) a monomer containing basic nitrogen groups, and (iii) a monomer comprising ethylene oxide chains containing between 2 and 9 repetitions of ethylene oxide. The mass average molecular mass of the polymer is greater than 100,000 so as to avoid elution problems.

Another filtration unit is described in U.S. Patent Application Publication No. 2006/0207937. Said unit comprises a filter coated with a polymer obtained by reacting a hydrophobic monomer and a hydrophilic monomer. The surface of the filter has a critical wetting surface tension (CWST) between 50 and 80 dyn/cm. For example, the polymer may be a copolymer of vinyl acetate and vinylpyrrolidone. The polymers have a mass average molecular mass (Mw) between 10,000 and 200,000 g/mol, preferably between 20,000 and 100,000 g/mol.

It has also been proposed in WO 2007/054638 to coat a leukocyte-removal medium with a linear polymer of the Poloxamer® type having a molar mass between 2,000 and 18,000 g/mol. This type of polymer coating, however, leads to elution problems.

SUMMARY

The present disclosure generally relates to the filtration of a fluid containing platelets. More specifically, the present disclosure relates to a filtration unit to selectively remove leukocytes from a fluid containing platelets, and systems comprising such a filtration unit.

The present disclosure relates to a surface treatment based on a polymer that is insoluble in water and to the use of that polymer in a filtration unit for selective leukocyte removal from a fluid containing platelets. One advantage of the polymer of the present disclosure is that the polymer is resistant to elution and steam sterilization while allowing for the retention of leukocytes and the passage of platelets through a surface treated with the polymer.

In one embodiment, the present disclosure provides a filtration unit to remove leukocytes from a fluid containing blood platelets comprising an outer casing comprising at least one inlet orifice and at least one outlet orifice, wherein the outer casing encloses a porous element arranged between the inlet orifice and the outlet orifice, wherein the porous element comprises a leukocyte-removal medium comprising a coating, wherein the coating comprises a polymer comprising a main hydrophobic chain and a hydrophilic poly (ethylene oxide) side chain and having a mass average molar mass in the range of from about 1,000 g/mol to about 20,000 g/mol, wherein the hydrophilic poly(ethylene oxide) side chain comprises from 9 to 50 ethylene oxide units, and wherein the mass percentage of the poly(ethylene oxide) side chain is less than about 50% of the mass average molar mass of the polymer.

Further objects and advantages will become clear from the following description.

DRAWINGS

Some specific example embodiments of the disclosure may be understood by referring, in part, to the following description and the accompanying drawings.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure generally relates to the filtration of a fluid containing platelets. More specifically, the present disclosure relates to a filtration unit to selectively remove leukocytes from a fluid containing platelets, and systems comprising such a filtration unit.

A fluid containing platelets is, for example, whole blood, a platelet-rich plasma (PRP), a platelet concentrate (PC), a pool of platelet concentrates, or a buffy coat, which is also referred to as a leuko-platelet layer. In certain embodiments, the filtration unit is designed to filter a pool of buffy coats obtained after combining from two to eight buffy coats produced from a donation of whole blood. In certain embodiments, a pool of five buffy coats is added to a solution for preserving platelets before being filtered. One example of a solution for preserving platelets is SSP+ available from Maco Pharma, France.

The filtration unit of the present disclosure enables selective leukocyte removal, in that it is capable of retaining leukocytes while allowing platelets to pass through the filtration unit. In certain embodiments, the filtration unit is able to obtain a number of leukocytes in the filtered fluid that is less than about $0.6 \times 10^{11}$ and to allow at least about 80% of the blood platelets present in the unfiltered fluid to pass through the filtration unit. In certain embodiments, the fluid filtered by means of the filtration unit comprises at least about $0.6 \times 10^{11}$ platelets for 40 ml of filtered fluid, less than about $1 \times 10^5$ leukocytes, and the recovery rate of the platelets is at least about 90%.

In certain embodiments, the fluid to be filtered may be a platelet concentrate. In such embodiments, the number of platelets in the platelet concentrate after filtration is at least about $2 \times 10^{11}$ platelets.

Figure 1:
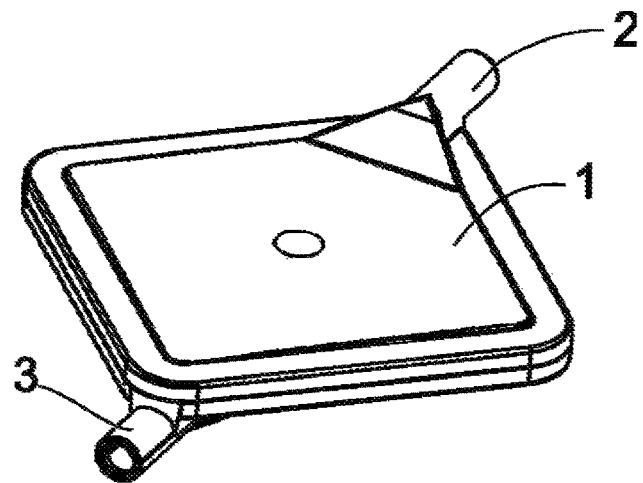
FIG. 1 shows a schematic perspective view of a filtration unit according to the present disclosure.
Figure 2:
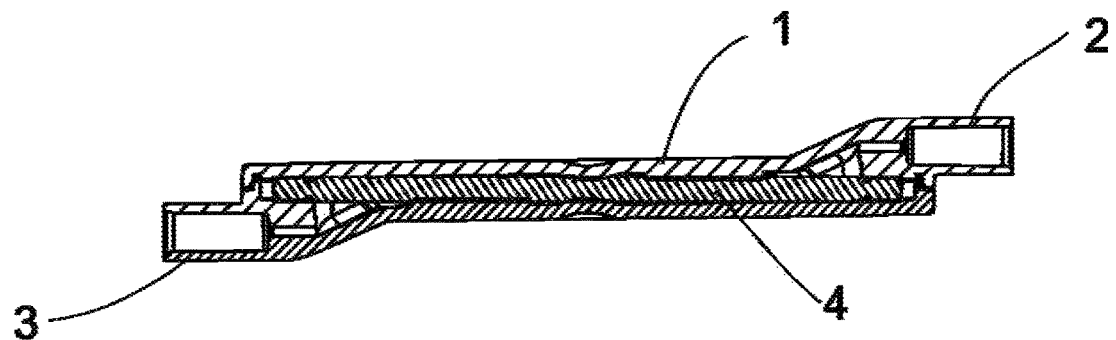
FIG. 2 shows a schematic cross-sectional view of the filtration unit of FIG. 1.

As illustrated in FIGS. 1 and 2, the filtration unit 1 comprises an outer casing comprising at least one inlet orifice 2 and at least one outlet orifice 3, the casing enclosing a porous element 4 arranged between said orifices 2, 3, said porous element 4 comprising a leukocyte-removal medium coated with a polymer.

The outer casing of the filtration unit is flexible, rigid or semi-rigid. The filtration unit is advantageously symmetrical, such that it can be mounted in any direction in a system of bags without affecting the filtration performance.

Due to its polymer coating, the leukocyte-removal medium is able to retain leukocytes by adsorption and/or by filtration of the leukocytes present in the fluid containing the platelets. The polymer coating of the leukocyte-removal medium also prevents platelets from adhering to its surface.

In a leukocyte-removal medium, the leukocytes are retained by at least one of the following mechanisms. The first mechanism is the adsorption of the leukocytes at the surface of the medium. The leukocytes are adsorbed over moderately hydrophobic cationic surfaces. The quality of the adsorption also depends on the contact surface available for the adsorption of the leukocytes. The second mechanism is sieving and depends primarily on the diameter of the pores of the leukocyte-removal medium. On the other hand, for selective filtration, the surface of the leukocyte-removal medium must be sufficiently hydrophilic so that the platelets do not adhere to its surface.

The leukocyte-removal medium of the filtration unit of the present disclosure comprises a coating comprising a polymer. The polymer comprises a main hydrophobic chain and a hydrophilic poly(ethylene oxide) side chain. This polymer is also referred to as a coating polymer. The coating polymer is a comb polymer formed of a main hydrophobic chain having at least one branching point which is the starting point of a linear hydrophilic side chain. This non-linear comb structure promotes the adsorption of the polymer at the surface of the leukocyte-removal medium. The hydrophobic chain of the coating polymer contributes to the adsorption of the leukocytes and to the retention of the coating polymer at the surface of the leukocyte-removal medium. The hydrophilic side chain of the coating polymer allows the leukocyte-removal medium to be sufficiently hydrophilic so as to prevent adhesion of the platelets.

The coating polymer generally has a mass average molar mass (Mw) in the range of from about 1,000 g/mol to about 20,000 g/mol. In certain embodiments, the coating polymer has a mass average molar mass less than about 10,000 g/mol. In certain embodiments, the coating polymer has a mass average molar mass in the range of from about 1,000 g/mol to about 5,000 g/mol. The mass average molar mass is determined for example by steric exclusion chromatography in tetrahydrofuran with a polystyrene calibration.

Each poly(ethylene oxide) side chain of the coating polymer comprises from 9 to 50 units of ethylene oxide, and the mass percentage of the poly(ethylene oxide) side chain is less than about 50% of the mass average molar mass of the polymer. The poly(ethylene oxide) side chain makes it possible to increase the passage of the platelets. Short chains of poly(ethylene oxide) containing less than 9 ethylene oxide units do not achieve a sufficient hydrophilic nature to hinder the adsorption of platelets, when the mass percentage of said poly(ethylene oxide) chain is less than about 50% of the mass average molar mass of the polymer. Long chains of poly(ethylene oxide) containing more than 100 ethylene oxide units form a random coil however which has steric repulsion capacity. This reduces the adsorption of cells at the surface of the leukocyte-removal medium, including the adsorption of leukocytes.

In certain embodiments, the poly(ethylene oxide) side chain(s) advantageously comprise(s) from 15 to 30 units of ethylene oxide. This side chain length does not prevent the leukocytes from adhering to the leukocyte-removal medium and also allows the surface of the leukocyte-removal medium to be passivated so that the platelets are not retained.

To obtain effective filtration while effectively retaining leukocytes, the coating polymer must not have an excessively high number of side chains so the adsorption of the leukocytes over the hydrophobic portions of the polymer is not disturbed. The mass percentage of the poly(ethylene oxide) side chain of the coating polymer is thus less than about 50% of the mass average molar mass of the polymer. In certain embodiments, the mass percentage of the poly(ethylene oxide) side chain is less than about 40% of the mass average molar mass of the coating polymer. In certain embodiments, the mass percentage of the poly(ethylene oxide) side chain is in the range of from about 10% to about 40% of the mass average molar mass of the coating polymer. Since the coating polymer is of low average molar mass and comprises few hydrophilic side chains, the hydrophobic chains of the polymer remain easily accessible so that the polymer adheres correctly to the leukocyte-removal medium, and the leukocytes are adsorbed over these hydrophobic chains. The mass composition of the polymer is determined for example by nuclear magnetic resonance (NMR) spectrometry of $^1$H.

For example, in the case of a polymer formed of a poly(ethylene oxide) methacrylate monomer unit and a methyl methacrylate monomer unit, the NMR of $^1$H makes it possible to calculate the ratio of methyl methacrylate to ethylene oxide by determining the ratio of the band intensities at 3.3 ppm characteristic of O—CH$_3$ groups of methyl methacrylate and at 3.6 ppm characteristic of O—CH$_2$ groups of ethylene oxide. Knowing the number of average ethylene oxide units in a poly(ethylene oxide) methacrylate unit, it is thus easy to calculate the molar composition of poly(ethylene oxide) methacrylate and methyl methacrylate. The knowledge of the molar masses of these two monomer units makes it possible to determine the mass composition of the polymer.

The polymolecularity index of the polymer is in the range of from about 1 to about 3, and in certain embodiments, in the range of from about 1 to about 2.5. The polymolecularity index is the ratio of mass average molar mass (Mw) to the number average molar mass (Mn) of the polymer. This index makes it possible to characterize globally the dispersity of the molar masses of a polymer. An index close to 1 means that all the molar chains of a polymer are of equal length. The number average molar mass is determined for example by steric exclusion chromatography in tetrahydrofuran with a polystyrene calibration.

In accordance with one embodiment of the present disclosure, the hydrophobic chain of the coating polymer derives from a hydrophobic monomer. Examples of suitable hydrophobic monomers include styrene and styrene compounds, vinyl compounds such as vinyl acetate, acrylate derivatives or methacrylate derivatives, and acrylamide derivatives. In certain embodiments, the hydrophobic monomer may be, for example, an alkyl acrylate or alkyl methacrylate, such as methyl methacrylate.

The hydrophilic side chain derives from a poly(ethylene oxide) macromonomer. Macromonomers are polymers or oligomers having a reactive end, for example, a polymerizable functional group, which allow it to react as a monomer. The polymerizable functional group can be selected from the (meth)acrylic, vinyl, and allyl groups.

In certain embodiments, the macromonomer of poly(ethylene oxide) is a methacrylate of poly(ethylene oxide), and the number of ethylene oxide units in the poly(ethylene oxide) chain is in the range of from 9 to 50.

In certain embodiments, the coating polymer is a copolymer of a hydrophobic monomer and a hydrophilic poly(ethylene oxide) macromonomer. For example, the copolymer can be obtained by copolymerization of a methyl methacrylate monomer and a poly(ethylene oxide) methacrylate monomer. The coating polymer of the present disclosure is advantageously insoluble in water, soluble in an alcoholic or ketone solvent, and resistant to steam sterilization.

To coat the leukocyte-removal medium with the coating polymer, an impregnation solution formed of the coating polymer as solute and an organic liquid as solvent is first prepared. The impregnation solution contains a low concentration of coating polymer. In particular, the quantity of polymer dissolved in the solvent is in the range of from about 5 g/L and to about 50 g/L, and in certain embodiments, in the range of from about 10 g/L to about 20 g/L. In certain embodiments, the organic liquid solvent is an alcoholic solvent, such as methanol or ethanol, or a ketone solvent, such as acetone or methyl ethyl ketone.

Figure 3:
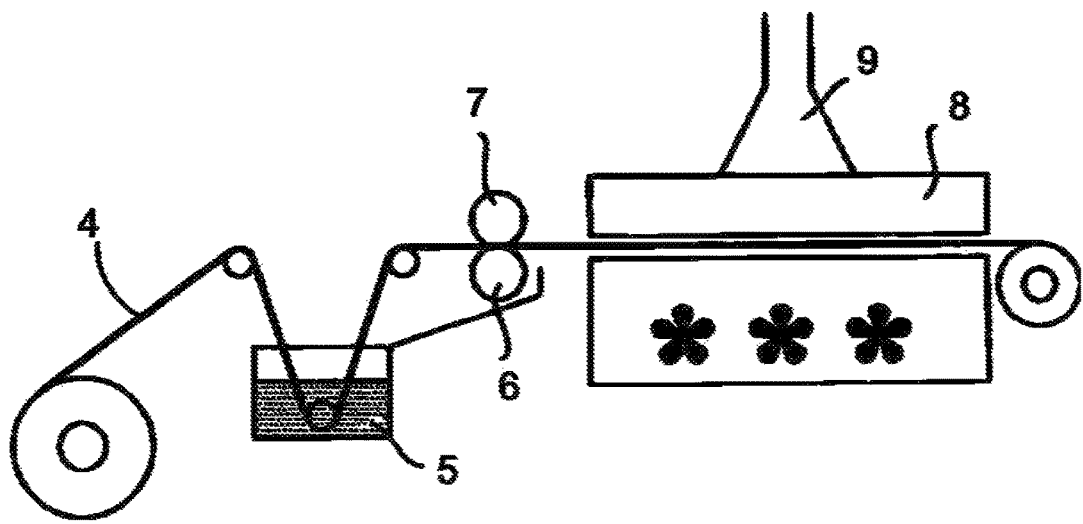
FIG. 3 illustrates an assembly enabling the coating of a leukocyte-removal medium according to the principle of pad drying.

In certain embodiments, the leukocyte-removal medium is coated using an assembly and a dry-padding principle. One example of such an assembly is shown in FIG. 3. The leukocyte-removal medium 4 is soaked in the impregnation solution 5. The excess impregnation solution on the leukocyte-removal medium is then expressed or wrung out by passing the medium between two rolls 6, 7 of which the pressure is from about 1 to about 5 bar. The leukocyte-removal medium 4 is then conveyed into a furnace 8 equipped with a mechanical ventilation system 9 so as to dry the medium by evaporation of the solvent of the impregnation solution. The speed, which is between 1 and 10 m/min, is controlled according to the nature and quantity of solvent carried by the leukocyte-removal medium.

The quantity of polymer deposited on the leukocyte-removal medium is in the range of from about 10 mg/g to about 50 mg/g of leukocyte-removal medium. This quantity is determined, for example, with the aid of a Soxhlet extraction apparatus then by evaporation of the solvent or by gas phase chromatography. The Soxhlet apparatus makes it possible to extract the solvent continuously from the coated polymer on the leukocyte-removal medium.

The leukocyte-removal medium coated with the polymer has a critical wetting surface tension (CWST) in the range of from about 65 to about 90 dyn/cm, and in certain embodiments, in the range of from about 70 to about 80 dyn/cm. This CWST is determined by the method described in document WO-8903717. A CWST in the range of from about 65 to about 90 dyn/cm means that the leukocyte-removal medium is effectively hydrophilic such that it can be wetted by blood. In order to avoid adhesion of the platelets to the leukocyte-removal medium, the surface of said medium must be hydrophilic. A CWST less than 65 dyn/cm does not prevent the adhesion of platelets. A CWST greater than 90 dyn/cm would prevent the adsorption of leukocytes. In certain embodiments, the CWST of the leukocyte-removal medium is approximately 72 dyn/cm.

The hydrophilic nature of the coating polymer comprising a hydrophobic chain and a hydrophilic poly(ethylene oxide) side chain depends not only on the mass percentage of the poly(ethylene oxide) chain in the coating polymer, but also on the average molar mass of the coating polymer. For example, a leukocyte-removal medium coated with a methyl methacrylate and poly(ethylene oxide) methacrylate copolymer with a molar mass of 1,100 g/mol has a CWST of 60 dyn/cm if the copolymer comprises 54% by mass of poly(ethylene oxide) and has a mass average molar mass of 49,800 g/mol, whereas it has a CWST of 72 dyn/cm if the copolymer comprises 30% by mass of poly(ethylene oxide) and has a mass average molar mass of 3,800 g/mol.

In certain embodiments, the leukocyte-removal medium comprises polyester fibers. The polyester fibers may be, for example, polybutylene terephthalate fibers or polyethylene terephthalate fibers.

In certain embodiments, the leukocyte-removal medium is formed of at least one layer of non-woven material. In certain embodiments, the leukocyte-removal medium comprises from 5 to 40 layers of non-woven material, and in certain embodiments, from 10 to 20 layers of non-woven material. In certain embodiments, the diameter of the fibers of the layer(s) of non-woven material is in the range of from about 0.3 µm to about 7 µm, with an average diameter in the range of from about 1 µm to about 3 µm. To mechanically retain the leukocytes, the average diameter of the pores of the layer of non-woven material is advantageously in the range of from about 3 µm to about 15 µm, and in certain embodiments, in the range of from about 7 µm to about 10 µm. With a quantity of polymer deposited on the leukocyte-removal medium in the range of from about 10 mg/g to about 50 mg/g of leukocyte-removal medium, the average diameter of the pores and the average diameter of the fibers of the layer(s) of non-woven material before and after coating remain substantially the same.

In certain embodiments, the porous element of the filtration unit further comprises a pre-filter and/or post-filter, which comprise at least one layer of non-woven material and which are arranged upstream and downstream of the leukocyte-removal medium respectively. These pre-filters or post-filters in particular have an average pore size diameter greater than that of the leukocyte-removal medium, for example in the range of from about 25 µm to about 50 µm. In certain embodiments, the pre-filters or post-filters comprise a polymer coating facilitating the passage of platelets. In certain embodiments, the pre-filters or post-filters do not include a polymer coating facilitating the passage of platelets.

Figure 4:
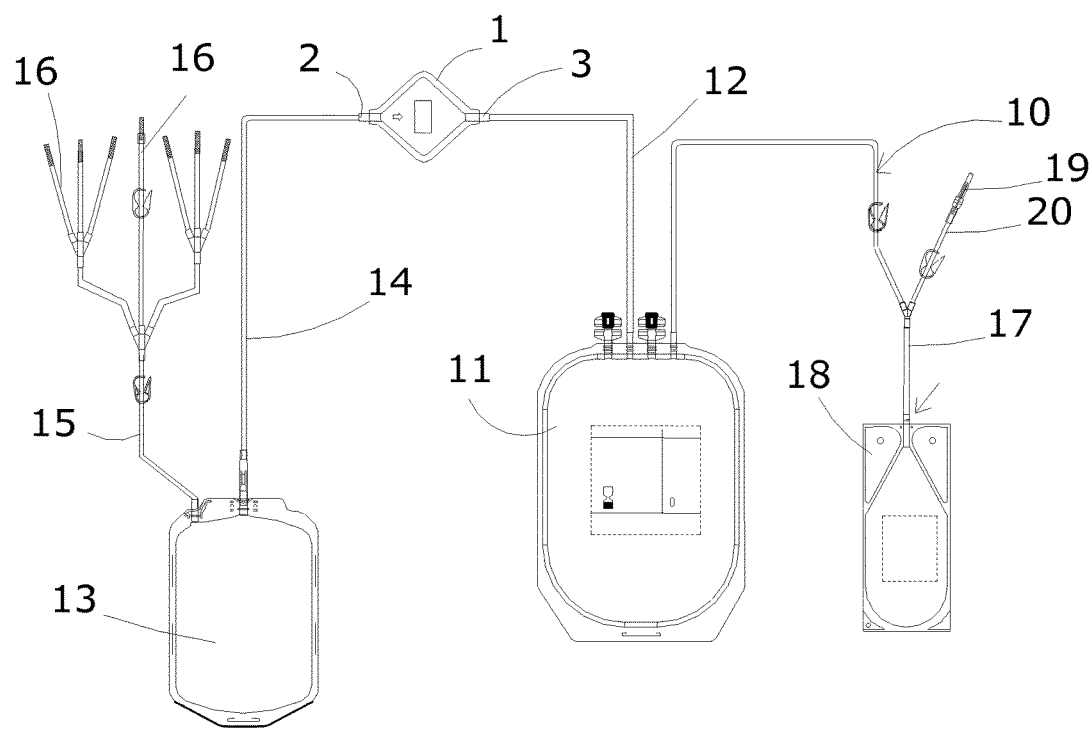
FIG. 4 illustrates one example of a system of bags including a filtration unit of the present disclosure.

As shown in FIG. 4, the present disclosure also relates to a system of bags 10 for removing leukocytes from a fluid containing blood platelets, comprising: a filtration unit 1, and a bag for collecting the filtrate 11, said bag 11 being connected, via a tube 12, to an outlet orifice 3 of the filtration unit 1.

A specific system of bags will now be described with reference to FIG. 4 for the preparation and the filtration of a pool of buffy coats.

The system of bags 10 comprises a pool bag 13 connected or designed to be connected via a first tube 14 to the filtration unit 1. The filtration unit 1 is connected via a second tube 12 to the bag 11 for collecting the filtrate. For the preparation of the pool of buffy coats, the pool bag 13 is fluidically connected to a set of tubes formed of a primary tube 15 and secondary tubes 16 branched from the primary tube. These secondary tubes 16 are designed to be connected in a sterile manner to at least two bags, each of which contains a buffy coat, and optionally to a bag containing an additional solution for preservation of platelets.

As shown in FIG. 4, in certain embodiments, the bag 11 for collecting the filtrate from filtration unit 1 is fluidically connected by means of a third tube 17 to a satellite bag 18 designed to receive the air present in the bag 11 for collecting the filtrate and/or designed to collect a sample of the fluid contained in the bag 11. To remove samples of the fluid contained in bag 11, the system of bags comprises a fourth tube 20, which is branched from the third tube 17, said fourth tube 20 being provided at its end with a sampling means 19. The sample removed is used for the detection of a bacterial contamination (Bact/Alert® system). The tubes of the system of bags 10 are each provided with a clip so as to control the flow of fluids within the system of bags.

A use of the system of bags 10 will now be described with reference to the system of bags in FIG. 4. Four to six bags containing a buffy coat are connected in a sterile manner. A sterile connection apparatus may be used to connect the bags containing buffy coats to the secondary tubes 16. One example of a sterile connection apparatus suitable for use is for example, a sterile connection apparatus of the SCD type available from Terumo. A bag of platelet preservation solution may also be connected in a sterile manner to one of the secondary tubes 16. One example of a solution for preserving platelets suitable for use is SSP+ available from Maco Pharma, France.

The buffy coats flow into the pool bag 13. The preservation solution is then transferred towards the pool bag 13. The set of tubes 15, 16 is then separated from the pool bag 13 by welding. The pool bag 13 is then centrifuged so as to obtain a sedimentary layer of red blood cells and a layer of supernatant of platelet concentrate. The pool bag 13 containing the layers of red blood cells and platelet concentrate is then pressed to send the platelet concentrate towards bag 11 for collecting the filtrate via the filtration unit 1 and to obtain a platelet concentrate from which the leukocytes have been removed. A press device may be used to press pool bag 13. One example of a press device suitable for use is of the Macopress Smart type, available from Maco Pharma, France.

To facilitate a better understanding of the present disclosure, the following examples of certain aspects of some embodiments are given. In no way should the following examples be read to limit, or define, the entire scope of the invention.

EXAMPLES

Example 1

Preparation of a Coating Polymer

A poly(ethylene oxide) methacrylate (molar mass: 475 g/mol; number of ethylene oxide units=9) was solubilized in ethanol before being copolymerized with methyl methacrylate. The copolymer (copolymer A) was lyophilized and dried at 100° C. under vacuum for 4 hours.

The copolymer A obtained was not soluble in water. Its molar mass was approximately 7,300 g/mol, and its polydispersity index was 2.4. The copolymer A comprises 45% by mass of poly(ethylene oxide) methacrylate and 55% by mass of methyl methacrylate.

Preparation of Impregnation Solution

The impregnation solution was prepared by solubilizing copolymer A in ethanol so as to obtain an impregnation solution comprising 96% by mass of ethanol and 4% by mass of copolymer A.

Coating

Fifteen layers of non-woven material made of polybutylene terephthalate (42 g/m$^2$, average diameter of pores 8.5 µm) were impregnated with the solution prepared above and in accordance with the pad-drying principle described above. The CWST of the layers was 72 dyn/cm.

The quantity of polymer deposited was approximately 20 mg of copolymer per gram of non-woven material.

Filtration

A filtration unit was produced comprising a leukocyte-removal medium formed of fifteen layers coated with the copolymer A as described above.

A platelet concentrate prepared from a pool of five buffy coats was filtered by means of the filtration unit.

The filtration lasted for 4 minutes and 50 seconds. The volume of platelet concentrate after filtration was 319 mL. The platelet concentrate contained $4.45 \times 10^{11}$ platelets after filtration (a recovery rate of 86%) and $1.18 \times 10^5$ white blood cells.

Example 2

Example 1 was repeated with a copolymer B obtained by copolymerization of a poly(ethylene oxide) methacrylate with a molar mass of 1100 g/mol and methyl methacrylate.

The copolymer B obtained was not soluble in water. Its molar mass was approximately 3,800 g/mol and its polydispersity index was 1.7. Copolymer B comprised 30% by mass of poly(ethylene oxide) methacrylate and 70% by mass of methyl methacrylate.

The filtration results were as follows: The filtration lasted for 5 minutes and 12 seconds. The volume of platelet concentrate after filtration was 310 ml. The platelet concentrate contained $3.5 \times 10^{11}$ platelets after filtration (a recovery rate of 83%) and $5.42 \times 10^4$ white blood cells.

The results of Examples 1 and 2 indicate that hydrophilic chains of greater length yet fewer in number have a similar efficacy for the non-adhesion of platelets, but allow better adhesion of leukocytes.

Example 3

Example 1 was repeated using a filtration unit comprising a leukocyte-removal medium formed of fifteen layers of non-woven material made of polybutylene terephthalate (52 g/m$^2$, average diameter of pores 10 µm), coated with the impregnation solution of copolymer A of Example 1.

The filtration results were as follows: The filtration lasted for 69 seconds. The volume of platelet concentrate after filtration was 265 ml. The platelet concentrate contained $2.59 \times 10^{11}$ platelets after filtrations (a rate of recovery of 89%) and $1.06 \times 10^5$ white blood cells.

Example 4

Example 3 was repeated with a copolymer C comprising a hydrophilic chain derived from a poly(ethylene oxide) methacrylate with a molar mass 1,100 g/mol and a hydrophobic poly(propylene oxide) chain.

The copolymer C obtained was not soluble in water. Its molar mass was approximately 51,000 g/mol and its polydispersity index was 1.5.

The filtration results were as follows: Filtration lasted for 54 seconds. The volume of platelet concentrate after filtration was 178 ml. The platelet concentrate after filtration contained $7.64 \times 10^{10}$ platelets (a recovery rate of 65%) and $1.42 \times 10^4$ white blood cells.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Unless the meaning is clearly to the contrary, all ranges set forth herein are deemed to be inclusive of the endpoints. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A filtration unit to remove leukocytes from a fluid containing blood platelets comprising:
    an outer casing comprising at least one inlet orifice and at least one outlet orifice, wherein the outer casing encloses a porous element arranged between the inlet orifice and the outlet orifice, wherein the porous element comprises a leukocyte-removal medium comprising a coating, wherein the coating comprises a polymer comprising a main hydrophobic chain and a hydrophilic poly(ethylene oxide) side chain and having a mass average molar mass in the range of from about 1,000 g/mol to about 5,000 g/mol, wherein the hydrophilic poly(ethylene oxide) side chain comprises from 9 to 50 ethylene oxide units, and wherein the mass percentage of the poly(ethylene oxide) side chain is less than about 50% of the mass average molar mass of the polymer.

2. The filtration unit of claim 1, wherein the main hydrophobic chain derives from a hydrophobic monomer selected from alkyl acrylates and alkyl methacrylates.

3. The filtration unit of claim 1, wherein the hydrophilic side chain derives from a poly(ethylene oxide) macromonomer.

4. The filtration unit of claim 3, wherein the poly(ethylene oxide) macromonomer is a poly(ethylene oxide) methacrylate.

5. The filtration unit of claim 1, wherein the hydrophilic poly(ethylene oxide) side chain comprises from 15 to 30 ethylene oxide units.

6. The filtration unit of claim 1, wherein the mass percentage of the poly(ethylene oxide) side chain is less than about 40% of the mass average molar mass of the polymer.

7. The filtration unit of claim 1, wherein the polymer has a polymolecularity index in the range of from about 1 to about 3.

8. The filtration unit of claim 1, wherein the quantity of polymer deposited on the leukocyte-removal medium is in the range of from about 10 mg/g to about 50 mg/g of leukocyte-removal medium.

9. The filtration unit of claim 1, wherein the leukocyte-removal medium has a critical wetting surface tension in the range of from about 65 to about 90 dyn/cm.

10. The filtration unit of claim 1, wherein the leukocyte-removal medium comprises at least one of polybutylene terephthalate fibers and polyethylene terephthalate fibers.

11. The filtration unit of claim 1, wherein the leukocyte-removal medium comprises at least one layer of non-woven material.

12. The filtration unit of claim 11, wherein the average diameter of the pores of the at least one layer of non-woven material is in the range of from about 3 μm to about 15 μm.

13. A system for removing leukocytes from a fluid containing blood platelets comprising:
   a filtration unit comprising an outer casing comprising at least one inlet orifice and at least one outlet orifice, wherein the outer casing encloses a porous element arranged between the inlet orifice and the outlet orifice, wherein the porous element comprises a leukocyte-removal medium comprising a coating, wherein the coating comprises a polymer comprising a main hydrophobic chain and a hydrophilic poly(ethylene oxide) side chain and having a mass average molar mass in the range of from about 1,000 g/mol to about 5,000 g/mol, wherein the hydrophilic poly(ethylene oxide) side chain comprises from 9 to 50 ethylene oxide units, and wherein the mass percentage of the poly(ethylene oxide) side chain is less than about 50% of the mass average molar mass of the polymer; and
   a first bag for collecting the fluid, said first bag being connected by a first tube to the outlet orifice of the filtration unit.

14. The system of claim 13 further comprising a second bag, said second bag being connected by a tube to the bag for collecting the fluid.

15. The system of claim 13, wherein the hydrophilic poly(ethylene oxide) side chain comprises from 15 to 30 ethylene oxide units.

16. The system of claim 13, wherein the mass percentage of the poly(ethylene oxide) side chain is less than about 40% of the mass average molar mass of the polymer.

17. The system of claim 13, wherein the quantity of polymer deposited on the leukocyte-removal medium is in the range of from about 10 mg/g to about 50 mg/g of leukocyte-removal medium.

18. The system of claim 13, wherein the leukocyte-removal medium has a critical wetting surface tension in the range of from about 65 to about 90 dyn/cm.

19. A filtration unit to remove leukocytes from a fluid containing blood platelets comprising:
   an outer casing comprising at least one inlet orifice and at least one outlet orifice, wherein the outer casing encloses a porous element arranged between the inlet orifice and the outlet orifice, wherein the porous element comprises a leukocyte-removal medium comprising a coating, wherein the coating comprises a comb polymer comprising a main hydrophobic chain and a hydrophilic poly(ethylene oxide) side chain branching from the main hydrophobic chain and having a mass average molar mass in the range of from about 1,000 g/mol to about 5,000 g/mol, wherein the hydrophilic poly(ethylene oxide) side chain comprises from 9 to 50 ethylene oxide units, and wherein the mass percentage of the poly(ethylene oxide) side chain is less than about 50% of the mass average molar mass of the polymer.

20. The system of claim 13, further comprising a second bag connected to the first bag by a second tube and a needle for collecting a sample from the second bag.

21. The system of claim 13, further comprising a second bag configured to receive air present in the first bag.

22. The filtration unit of claim 1, wherein the polymer is a copolymer of a hydrophobic polymer and a hydrophilic (polyethylene oxide) macromonomer.

\* \* \* \* \*